United States Patent [19]

Lee et al.

[11] Patent Number: 5,370,882
[45] Date of Patent: Dec. 6, 1994

[54] TASTE-ENHANCEMENT OF SODIUM CHLORIDE-REDUCED COMPOSITIONS

[75] Inventors: Eldon C. Lee, New Milford; John S. Tandy, Litchfield, both of Conn.

[73] Assignee: Nestec S.A., Vevey, Switzerland

[21] Appl. No.: 9,325

[22] Filed: Jan. 26, 1993

[51] Int. Cl.⁵ .......................... A23L 1/22; A23L 1/23; A23L 1/237
[52] U.S. Cl. ........................... 426/96; 426/97; 426/302; 426/649; 426/650
[58] Field of Search .................. 426/96, 97, 650, 649, 426/302

[56] References Cited

U.S. PATENT DOCUMENTS

| | | | |
|---|---|---|---|
| 2,471,144 | 5/1949 | Davy | 426/649 |
| 2,601,112 | 6/1952 | Freedman | 426/649 |
| 3,622,350 | 11/1971 | Hammes . | |
| 3,782,974 | 1/1974 | Lontz et al. | 426/649 |
| 4,068,006 | 1/1978 | Moritz . | |
| 4,243,691 | 1/1981 | Mohlenkamp, Jr. et al. | 426/649 |
| 4,340,614 | 7/1982 | Pich et al. | 426/649 |
| 4,451,494 | 5/1984 | Roan, III | 426/649 |
| 4,997,672 | 3/1991 | DeSimone et al. | 426/649 |
| 5,139,794 | 8/1992 | Patel et al. | 426/96 |

Primary Examiner—Donald E. Czaja
Assistant Examiner—Mary S. Mims
Attorney, Agent, or Firm—Vogt & O'Donnell

[57] ABSTRACT

The taste of foods and beverages containing less than a normal amount of sodium chloride is enhanced by addition of a food-acceptable encapsulated ammonium salt. Food-acceptable carrier agents for encapsulating food-acceptable ammonium salts include maltodextrin, gum arabic and gelatinized starches, in particular, starches which have a high amylopectin content, and in particular, a gelatinized starch hydrolysate debranched at 1,6-alpha-D-glycosidic linkages. The ammonium salts are usefully prepared with ammonia recovered during spray-drying of fermented soy sauce and by recovering ammonia formed by acid hydrolysis of a protein.

28 Claims, No Drawings

TASTE-ENHANCEMENT OF SODIUM CHLORIDE-REDUCED COMPOSITIONS

BACKGROUND OF THE INVENTION

The present invention relates to salt taste-enhancers more particularly to encapsulated ammonium salts as salt taste-enhancers for food compositions.

Excessive dietary sodium ion intake, the primary source of which is sodium chloride or table salt in foods, has long been associated with a number of health problems such as hypertension. It is generally recognized that the sodium ion intake of most persons is in excess of minimal physiological needs of the body. Consequently, a marked reduction in sodium consumption is recommended for most persons. However, the inclusion of sodium chloride in the diet contributes a good deal to the palatability of foods, and food without salt is perceived to be tasteless, flat and unpalatable.

Heretofore, a number of sodium-free compositions have been suggested as salt substitutes to replace sodium chloride in foods while retaining the palatability of the food.

Examples of such salt substitutes are disclosed in U.S. Pat. Nos. 2,471,144; 2,601,112; 3,782,974; 4,243,691; 4,340,614; and 4,451,494. Among the most popular salt substitutes are potassium chloride, ammonium salts such as ammonium chloride and mixtures thereof. However, such salt substitutes suffer from a number of disadvantages, including off-taste or bitter flavor, a taste perception different than sodium chloride and a salty impression much less from that of sodium chloride. In particular, ammonium salts are hygroscopic and have a sour aftertaste. Typically, a number of other components must be included to mask the bitterness which a salt substitute, such as potassium or ammonium chloride imparts, such as a combination with potassium chloride of calcium and magnesium formate and citrate salts, sugar, choline citrate and hydrolysed animal protein.

Another procedure which has been suggested for reducing sodium ion intake is to incorporate salt taste-enhancers in foods and beverages. That is, compounds, which potentiate or amplify the taste of sodium chloride in foods and beverages so that the sodium chloride content thereof may be reduced without adversely affecting the desired salty taste of the food. For example, U.S. Pat. No. 4,997,672 and the prior art discussed therein, disclose the use of substances such as cationic surfactants, bretylium tosylate, certain polypeptides, and the like, as salt taste-enhancers.

SUMMARY OF THE INVENTION

We have found that an encapsulated ammonium salt, when added to a food or beverage containing less than a normal amount of sodium chloride, will enhance or potentiate the salty taste of the food or beverage.

Accordingly, the present invention provides a composition enhanced in sodium chloride taste which comprises a food or beverage containing a less than normal amount of sodium chloride, and a sodium chloride taste potentiating amount of an encapsulated ammonium salt.

The salt taste-enhancers of the present invention allow the sodium chloride content of a food or beverage to be reduced without adversely affecting the desired salty taste of the product. It is to be understood that the salt taste-enhancers of this invention are not salt substitutes and do not completely replace sodium chloride in the food or beverage. Rather, they are saltiness enhancers and require a minimum level of sodium chloride in the food or beverage of about 0.20% in order to potentiate the sodium chloride taste in the product.

Accordingly, the present invention provides, in addition, a process for potentiating the salty taste of a food or beverage containing a less than a normal amount of sodium chloride by adding to the food or beverage a sodium chloride taste potentiating amount of an encapsulated ammonium salt.

The present invention also provides a process for preparing a salty tasting food or beverage containing a reduced amount of sodium chloride which comprises formulating a food or beverage with an amount of sodium chloride less than is necessary to achieve a desired salty taste in the food or beverage, and potentiating the sodium chloride taste by adding an encapsulated ammonium salt to the food or beverage of reduced sodium chloride content.

DETAILED DESCRIPTION OF THE INVENTION

Examples of ammonium salts which may be encapsulated are food acceptable salts such as the chlorides, phosphates, citrates, lactates, tartrates, fumarates, adipates, malates, succinates and gluconates. One useful source of ammonia which can be converted into an ammonium salt to be encapsulated is ammonia recovered from fermented soy sauce during spray drying.

However, one especially advantageous source of ammonia which can be converted into an ammonium salt is formed during protein hydrolysis, e.g., from the evaporator condensate waste stream obtained in the production of acid hydrolysed proteins.

In this acid hydrolysis process, vegetable plant or animal proteins derived from corn, soy, wheat, rice, yeast, peanut or casein are commonly used as starting protein sources and are usually obtained as a result of the separation of the protein fraction during milling of grains or following solvent extraction of oils. The protein contents of these raw materials may range from 40% to 90% with a general average of about 60%. Normally, the protein source is hydrolysed with hydrochloric acid having a concentration of about 20% by weight at a temperature from about 120°–135° C. over a period from about 5 to 8 hours and elevated pressure up to 30 psig (2 bar).

Following hydrolysis, the slurry is neutralised with a suitable alkaline material such as sodium hydroxide or sodium carbonate to a pH of from 5.0 to 5.3, and the residual unhydrolysed material (lignin, humin) is filtered out. The slurry may be decolourised prior to filtration or the filtrate following filtration may be decolourised by conventional means, e.g., activated carbon, absorption resins.

Following filtration of the unhydrolysed material and salts formed, the filtered liquid, containing about 42% solids may be further concentrated to pastes by a vacuum evaporator, and the pastes then are dried in a vacuum oven. Ammonia is removed during vacuum evaporation and may be trapped in the distillate by a condensor forming an evaporator condensate waste stream containing dilute ammonia.

The encapsulated ammonium salt may be produced from the evaporator condensate waste stream by an evaporator system or by a degassifier system to give a concentrated ammonium salt which may then be spray dried with the encapsulating agent.

The present invention thus further provides an encapsulated ammonium salt wherein the ammonium salt is derived from ammonia formed during protein hydrolysis.

In the evaporator system, the encapsulated ammonium salt taste-enhancer is prepared by neutralising the evaporator condensate waste stream with an acid (e.g., hydrochloric acid), concentrating using a vacuum evaporator, purifying with activated carbon, filtering and then spray drying the filtrate with an encapsulating carrier.

In the degassifier system, the encapsulated ammonium salt taste-enhancer is prepared by heating the evaporator condensate waste stream to a temperature of from 30° C. to just below the boiling point of water, preferably from 35° C. to 96° C. and more preferably from 40° C. to 90° C., through a heat exchanger, raising the pH to above 9, preferably above 10 and especially 11 with alkali, injecting through a nozzle into a packed tower followed by a forced air degassifier, trapping the volatiles in an acid solution, e.g., concentrated HCl (32%), phosphoric, tartaric, lactic or citric acid to form a salt solution and then, spray drying the salt solution, containing usually from 15% to 25% by weight of solids, with an encapsulating carrier.

Encapsulating agents that may be used include maltodextrin, gum arabic, and gelatinised starches which are advantageously hydrolysed.

The starches are preferably starches with a high amylopectin content such as waxy cereal starches, e.g., waxy maize starch and waxy rice starch. The starches are conveniently cooked to be gelatinized before hydrolysis and, if desired, they may be modified, preferably at the raw stage. The starches may be hydrolyse at their 1, 6-alpha-D-glycosidic linkages.

The hydrolysing enzyme may, for instance, be an isoamylase (1, 6-alpha-D-glucosidase), a debranching enzyme which specifically hydrolyses the 1, 6-alpha-D-glycoside bonds of branch-chain amylopectin to form amylose without formation of reducing sugars and/or oligosaccharides. Isoamylases may be obtained from broad beans (R-enzyme) or from the fermentation of yeast and bacterial species such as Pseudomonas and Cytophaga. The isoamylase, Amano DB-250 (Amano Enzyme USA Co. Ltd.) is obtained by a fermentation process from a selected strain of Bacillus sectorrams. Another suitable hydrolysing enzyme is a heat-stable pullulanase debranching enzyme, pullulan 6-glucanohydrolase, which hydrolyses the 1, 6-alpha-D-glycosidic linkages of amylopectin as well as pullulan, a linear polysaccharide composed of maltotriose units linked by 1,6-alpha-D-glycosidic bonds. The pullulanase, Amano pullulanase #3 (Amano Enzyme USA Co., Ltd) is obtained by a fermentation process from a selected strain of Aerobacter sp. The pullulanase, Novo promozyme 200L (Novo Nordisk A/S) is obtained from a selected strain of Bacillus acidopullulyticus by submerged fermentation and is a U.S. food grade enzyme, which has been used for preparing the debranching starch hydrolysate as the encapsulating agent.

The encapsulated ammonium salt taste-enhancers of the present invention are effective in potentiating or amplifying the salty taste of foods and beverages even when incorporated at relatively low levels. For example, the salty taste of foods and beverages is significantly enhanced by the incorporation therein of encapsulated ammonium salt containing the ammonium salt in an amount of from 0.05 to 0.75%, preferably from 0.1 to 0.5% and especially from 0.15 to 0.3% by weight based on the weight of food or beverage. If the encapsulated ammonium salt contains about 50% by weight of the ammonium salt, then the levels of the encapsulated ammonium salt are from 0.1 to 1.5%, preferably from 0.2 to 1.0% and especially from 0.3 to 0.6% by weight based on the weight of food or beverage.

A salt taste potentiating amount of encapsulated ammonium salt is effective in potentiating the sodium chloride taste in a wide variety of foods and beverages containing a less than normal amount of sodium chloride, but having a minimum level of sodium chloride of at least about 0.20%. For example, the salty taste of foods such as low sodium chicken broth, soups, salad dressing, sauces, mayonnaise, cooked ground beef, oat-meal, and the like, containing a less than normal amount of sodium chloride, is significantly enhanced by the addition of encapsulated ammonium salt in the amounts indicated above. Greater amounts up to about 3% or more of the encapsulated salt may, of course, be used, but, preferably, the amount of encapsulated salt used is from 0.1% to 1.5% by weight based on the weight of food or beverage as indicated above.

EXAMPLES

The following Examples further illustrate the present invention. Parts and percentages are by weight when not stated.

Example 1

Waxy maize starch (20%) was dispersed in an aqueous solution, cooked to 95° C., and then cooled to 40° C. in a Brabender amylograph. Amano pullulanase #3 (Amano Enzyme USA Co., Ltd) (3,000 units/ml) was added at the use level of 0.2% based on starch. The hydrolysis reaction was carried out with agitation at a constant temperature, 40° C. and viscosity is monitored during reaction. HPP evaporator condensate (100 kg, ammonium nitrogen 0,210%) was neutralized with 32% hydrochloric acid, concentrated using a vacuum evaporator to 3kg, purified with activated carbon (100 g Nuchar SA) at 70° C. for 45 min., and then filtered. The filtrate (ammonium nitrogen 5.79%; NH4Cl 22.12%) was mixed with the above starch hydrolysate (2.27 kg), and then spray-dried with inlet air temperature of 150° C. and outlet temperature of 90° C. to a finished powder product (NH4Cl48.0%). The recovery yield of ammonium chloride during spray drying was 68.7%. The product gave an excellent clean, white powder with low hygroscopicity.

Example 2

Waxy rice starch (20%) was used instead of waxy maize starch as in Example 1, and isoamylase alpha-1, 6-D-glucosidase (Amano DB-250-Amano Enzyme USA Co., Ltd) (300 units/ml) was used instead of pullulanase at the use level of 2% based on starch. The resulting finished powder product contained 50.0% NH4Cl. The recovery yield of ammonium chloride was 74.0%. The finished product gave an excellent clean, white and low hygroscopic powder.

Example 3

A typical low-cost cheese sauce contains approximately 1.6% by wt. sodium chloride. In order to demonstrate the effectiveness of the salt taste-enhancers of the present invention, a comparable low-cost cheese sauce was formulated containing 0.5% sodium chloride, and was used as a control. To one aliquot of this control cheese sauce was added 0.40% by weight of the spray-dried encapsulated ammonium chloride (48% NH₄Cl by weight) prepared in Example 1. The control cheese sauce and the sauce to which the salt taste-enhancers had been added were then evaluated by a sensory panel consisting of eight trained judges who were of the opinion that the salt taste-enhancer significantly amplified the sodium chloride taste.

Example 4

3.41 g of a low sodium chicken base containing 41 mg Na/g base and 1.69 g of a low sodium beef base containing 83 mg Na/g base were used as test media each in a serving portion of 100 g.

Control samples were made by adding NaCl and KCl to the test media, and a sample according to the present invention was made by adding, 0.40 g of the spray-dried encapsulated ammonium chloride (48% NH₄Cl by weight) as prepared in Example 1. The amounts of NaCl and KCl, as well as the sodium content / 100 g serving portion, are given in the following Table 1.

TABLE 1

| Sample | Sodium content 100 g serving | Chicken broth | Beef broth |
| --- | --- | --- | --- |
| 1) Test medium | 140 mg | 3.41 g base | 1.69 g base |
| 2) Control with NaCl added | 280 mg | 3.41 g base + 0.36 g NaCl | 1.69 g base + 0.36 g NaCl |
| 3) Encapsulated ammonium salt | 140 mg | 3.41 g base + 0.40 g | 1.69 g base + 0.40 g |
| 4) KCl | 140 mg | 3.41 g base + 0.46 g | 1.69 g base + 0.46 g |

A sensory panel judged that the encapsulated ammonium salt significantly amplified the sodium chloride taste. The sample (3) gave comparable salt taste to the control sample (2) and gave better salt taste than the potassium chloride sample (4), which had an undesirable aftertaste.

We claim:

1. A food which has a sodium chloride content of at least about 0.20% by weight and which contains a food-acceptable ammonium salt encapsulated in a food-acceptable carrier agent in an amount to enhance salt taste of the food.

2. A food according to claim 1 wherein the carrier agent is selected from the group consisting of maltodextrin, gum arabic and gelatinized starch.

3. A food according to claim 1 wherein the carrier agent is a gelatinized starch hydrolysate debranched at 1,6-alpha-D-glycosidic linkages.

4. A food according to claim 1 wherein the food contains the ammonium salt in an amount of from 0.05% to 0.75% by weight based on the weight of the food.

5. A food according to claim 1 wherein the food contains the ammonium salt in an amount of from 0.1% to 0.5% by weight based on the weight of the food.

6. A food-acceptable ammonium salt encapsulated in a gelatinized starch hydrolysate debranched at 1,6-alpha-D-glycosidic linkages.

7. A process for enhancing a salt taste of foods and beverages comprising adding a food-acceptable ammonium salt encapsulated in a food-acceptable carrier agent to an edible composition, wherein the composition is selected from the group consisting of foods and beverages and contains at least about 0.20% sodium chloride by weight, in an amount to enhance salt taste of the composition.

8. A process according to claim 7 wherein the carrier agent is selected from the group consisting of maltodextrin, gum arabic and gelatinized starch.

9. A process according to claim 7 wherein the carrier agent is gelatinized starch hydrolysate debranched at 1,6-alpha-D-glycosidic linkages.

10. A process according to claim 7 wherein the encapsulated salt is added in an amount so that the edible composition contains the ammonium salt in an amount of from 0.05% to 0.75% by weight based on the weight of the composition.

11. A process according to claim 7 wherein the encapsulated salt is added in an amount so that the edible composition contains the ammonium salt in an amount of from 0.1% to 0.5% by weight based on the weight of the composition.

12. A process according to claim 7 wherein the ammonium salt has a salt anion selected from the group consisting of chloride, phosphate, citrate, lactate, tartrate, fumarate, adipate, malate, succinate and gluconate.

13. A process for preparing an encapsulated ammonium salt comprising enzymatically hydrolyzing a gelatinized starch with an enzyme selected from the group consisting of isoamylase and pullulanase to obtain a starch hydrolysate and encapsulating a food-acceptable ammonium salt in the hydrolysate.

14. A process according to claim 13 wherein the ammonium salt is encapsulated by spray-drying.

15. A process according to claim 13 wherein the starch which is hydrolyzed is a gelatinized waxy cereal starch.

16. A process for utilizing ammonia recovered during spray-drying fermented soy sauce comprising spray-drying fermented soy sauce and recovering ammonia during the spray-drying, converting the ammonia recovered into an ammonium salt and then encapsulating the salt in a food-acceptable carrier agent.

17. A process according to claim wherein the carrier agent is selected from the group consisting of maltodextrin, gum arabic, and gelatinized starch.

18. A process according to claim 16 wherein the carrier agent is a gelatinized starch hydrolysate debranched at 1,6-alpha-D-glycosidic linkages.

19. A process for utilizing ammonia formed during acid hydrolysis of a protein comprising recovering ammonia formed by acid hydrolysis of a protein, converting the ammonia recovered into an ammonium salt and then encapsulating the salt with a food-acceptable carrier agent.

20. A process according to claim 19 wherein the carrier agent is selected from the group consisting of maltodextrin, gum arabic, and gelatinized starch.

21. A process according to claim 19 wherein the carrier agent is a gelatinized starch hydrolysate debranched at 1,6-alpha-D-glycosidic linkages.

22. A process according to claim 19 wherein the ammonia is recovered from an evaporator condensate waste stream.

23. A process for obtaining ammonia and preparing an encapsulated ammonium salt comprising:
   hydrolyzing a protein with an acid to obtain a hydrolysate;
   vacuum evaporating the hydrolysate and obtaining a waste stream condensate containing ammonia;

neutralizing the condensate with an acid to obtain a neutralized condensate;

evaporatively concentrating the neutralized condensate to obtain a concentrate;

treating the concentrate with activated carbon to obtain a purified concentrate;

filtering the purified concentrate to obtain a filtrate; and spray-drying the filtrate together with an encapsulation carrier agent.

24. A process according to claim 23 wherein the encapsulation carrier is selected from the group consisting of maltodextrin, gum arabic, and gelatinized starch.

25. A process according to claim 23 further comprising hydrolyzing a starch with an enzyme selected from the group consisting of an isoamylase and a pullulanase to obtain the encapsulating carrier agent.

26. A process for obtaining ammonia and preparing an encapsulated ammonium salt comprising:

hydrolyzing a protein with an acid to obtain a protein hydrolysate;

vacuum evaporating the hydrolysate and obtaining a waste stream condensate containing ammonia;

heating the condensate to a temperature of from 30° C. to below 100° C. in a heat exchanger;

adding an alkali to the heated condensate to obtain a pH-adjusted condensate having a pH of above 9 injecting the pH-adjusted condensate into a packed tower and into a forced air degassifier and trapping condensate volatiles in an acid solution to obtain a salt solution; and spray-drying the salt solution with an encapsulation carrier agent.

27. A process according to claim 26 wherein the encapsulation carrier is selected from the group consisting of maltodextrin, gum arabic, and gelatinized starch.

28. A process according to claim 26 further comprising hydrolyzing a starch with an enzyme selected from the group consisting of an isoamylase and a pullulanase to obtain the encapsulating carrier agent.

* * * * *

UNITED STATES PATENT AND TRADEMARK OFFICE
CERTIFICATE OF CORRECTION

PATENT NO. : 5,370,882
DATED : December 6, 1994
INVENTOR(S) : Eldon C. LEE, et al.

It is certified that error appears in the above-indentified patent and that said Letters Patent is hereby corrected as shown below:

Column 1, line 31, delete --than-- and insert therefor --from-- and then, insert a comma after "chloride".

Column 1, line 32, delete "from".

Column 6, line 41, (line 1 of claim 17), after "claim", insert --16--.

Column 8, line 8 (line 10 of claim 26), insert a semi-colon after "9".

Signed and Sealed this

Seventh Day of March, 1995

Attest:

BRUCE LEHMAN

Attesting Officer    Commissioner of Patents and Trademarks